(12) United States Patent
March et al.

(10) Patent No.: US 7,348,581 B2
(45) Date of Patent: Mar. 25, 2008

(54) UV LIGHT-EMITTING DIODES AS A RADIATION SOURCE IN A DEVICE FOR THE ARTIFICIAL WEATHERING OF SAMPLES

(75) Inventors: Peter March, Frankfurt am Main (DE); Bernd Rudolph, Alzenau (DE)

(73) Assignee: Atlas Material Testing Technology GmbH (DE)

( * ) Notice: Subject to any disclaimer, the term of this patent is extended or adjusted under 35 U.S.C. 154(b) by 560 days.

(21) Appl. No.: 10/968,350

(22) Filed: Oct. 20, 2004

(65) Prior Publication Data

US 2005/0087768 A1    Apr. 28, 2005

(30) Foreign Application Priority Data

Oct. 27, 2003    (DE)    ................ 103 50 020

(51) Int. Cl.
*G01N 17/00*    (2006.01)
(52) U.S. Cl. ............ 250/504 R; 73/865.6; 73/866
(58) Field of Classification Search ............ 250/504 R
See application file for complete search history.

(56) References Cited

U.S. PATENT DOCUMENTS

| | | | | |
|---|---|---|---|---|
| 4,012,954 A | * | 3/1977 | Klippert | ............ 73/150 R |
| 5,854,433 A | | 12/1998 | Patel et al. | |
| 5,898,816 A | * | 4/1999 | Heeger et al. | ............ 392/408 |
| 6,626,052 B1 | * | 9/2003 | Martin et al. | ............ 73/865.6 |
| 2002/0093649 A1 | | 7/2002 | Brass | |
| 2002/0187070 A1 | | 12/2002 | Mori et al. | |
| 2004/0075065 A1 | * | 4/2004 | Spivak | ............ 250/504 R |

FOREIGN PATENT DOCUMENTS

| | | |
|---|---|---|
| DE | 25 02 239 | 7/1976 |
| DE | 195 26 368 A1 | 1/1997 |
| EP | 1 248 097 | 10/2002 |
| GB | 2 168 493 A | 6/1986 |
| JP | 03-34820 | 5/1991 |
| JP | 2001-229722 | 8/2001 |
| JP | 2002-184209 A1 | 6/2002 |
| WO | 2002-012127 | 2/2002 |
| WO | WO 03/065032 A2 | 8/2003 |

* cited by examiner

*Primary Examiner*—Nikita Wells
*Assistant Examiner*—James J Leybourne
(74) *Attorney, Agent, or Firm*—Vedder Price P.C.

(57) ABSTRACT

The usual xenon radiation source in conventional weathering testers is replaced by UV light-emitting diodes (LEDs) (6). These can be used to provide a good approximation of the UV component of the solar spectrum, in particular when different types of UV light-emitting diodes (6) with different emission characteristics are employed. Optionally, further light-emitting diodes in the visible spectral range may also be used in order to cover other parts of the solar spectrum. The light-emitting diodes (6) may be mounted on a flexible printed circuit board (5), which may in turn be fitted on a tubular holding body (4). The flexible printed circuit board carrying the light-emitting diodes may also be placed on other substrates (7) which are pliable in a geometrically stable way, so that that they can be arranged at a uniform distance from material samples with a particular surface topology, in order to obtain uniform exposure.

14 Claims, 2 Drawing Sheets

UV LIGHT-EMITTING DIODES AS A RADIATION SOURCE IN A DEVICE FOR THE ARTIFICIAL WEATHERING OF SAMPLES

The present invention relates to a device for the artificial weathering of samples according to the precharacterizing clause of Patent Claim 1. The weathering-dependent ageing of a sample, in particular of a flat material sample, is evaluated in such devices by exposing the sample to artificial weathering. To that end, such devices usually have a weathering chamber which contains holding means for holding samples to be weathered and a radiation source for applying radiation to the samples, in particular UV radiation.

Such devices for the artificial weathering of samples are intended to estimate the lifetime of materials which are constantly exposed to natural weather conditions during their use, and which therefore suffer from climatic effects such as sunlight, solar heat, moisture and the like. In order to obtain a good simulation of the natural weathering situation, the spectral energy distribution of the light generated in the device should correspond as closely as possible to that of natural solar radiation, for which reason xenon radiators are used as radiation sources in such devices. An accelerated ageing test of the materials is essentially achieved by much more intense irradiation of the samples compared with natural conditions, which speeds up the ageing of the samples. In this way, a prediction of the long-term ageing of a material sample can be made after a comparatively short time.

A large number of the samples studied in artificial weathering devices consist of polymeric materials. Their deterioration due to weathering is essentially caused by the UV component of solar radiation. The primary photochemical processes which take place during this, that is to say the absorption of photons and the generation of excited states or free radicals, are independent of temperature. The subsequent reaction steps with the polymers or additives, however, may be temperature-dependent so that the observed ageing of the materials is also temperature-dependent.

A xenon lamp is normally used as the radiation source in the weathering testers of the prior art. Although such a lamp is known to be able to simulate the solar spectrum very well, the emitted radiation nevertheless has a relatively high spectral component in the infrared spectral range, which needs to be suppressed by filters in order to prevent excessive heating of the samples. Furthermore, a commercially available xenon radiation source only has a lifetime of about 1500 hours.

A halogen lamp may also be used as the radiation source, although this has the disadvantage that it is not adjustable, or can only be adjusted to a minor extent. The same applies to fluorescent lamps, which likewise have already been used as radiation sources in weathering testers and which also have the disadvantage of a relatively short lifetime.

All of the aforementioned radiation sources furthermore have the disadvantage that they are not spectrally modifiable. But it is often useful to study the ageing of a material sample as a function of radiation in a limited wavelength range. For this purpose, admittedly, it is known to resolve the radiation of a xenon lamp into its spectral components by using a prism or grating before sending it onto the sample: the different parts of the sample are then exposed to radiation with a different wavelength and the property changes at different points of the sample can be unequivocally assigned to the wavelength of the incident radiation. This, however, needs relatively long exposure times since the spectral exposure level on the sample itself is relatively low.

Another disadvantage of the aforementioned conventional radiation sources in weathering testers, owing the way in which they are designed and operated, is that they are relatively unwieldy and, for example, modified conditions in respect of the sample surfaces of the material samples to be exposed cannot therefore be accommodated.

It is therefore an object of the present invention to provide a device for the artificial weathering of samples, in which the spectral and spatial features of the radiation source and the radiation emitted by it can be adapted more flexibly and, in particular, modified situations of the samples to be exposed can be accommodated better.

This object is achieved by the characterizing features of Patent Claim 1. The dependent claims relate to preferred embodiments and refinements.

Accordingly, the invention relates to a device for the artificial weathering of samples, having a weathering chamber which contains holding means for holding samples to be weathered and a UV radiation arrangement for applying UV radiation to the samples. The invention is essentially characterized in that the UV radiation arrangement comprises an arrangement of UV light-emitting diodes (LEDs). The invention therefore makes it possible to use of the availability of UV light-emitting diodes which has occurred in recent years for a weathering tester, in particular ones which are based on GaN. GaN LEDs can now satisfactorily cover the entire UV range of the solar spectrum. The obtainable radiation densities are already so high that the radiation power of a conventional xenon lamp can readily be achieved by a multiple arrangement of UV LEDs.

The intended UV spectrum depends only on the band gap of the semiconductor materials used in the LEDs. Additional undesired spectral components, such as infrared spectral components, are therefore not produced at all.

Another advantage is that the light intensity of the UV radiation which is generated can be adjusted very easily by means of the current delivered to the LEDs. The emission spectrum can also be altered to a limited extent by adjusting the current.

Owing to the compact nature of the LEDs, they can be arranged in the form of LED arrays. By mounting them on flexible printed circuit boards, it is also possible for geometrically non-planar samples to be exposed almost uniformly, or for a number of samples inside the weathering chamber to be exposed uniformly. Virtually any irradiation surfaces can be achieved since LED arrays are relatively easy to scale.

LEDs are furthermore known to have long lifetimes, of the order of 1500 hours or more.

Spectral modification of such a UV radiation arrangement can be achieved by providing a plurality of different types of light-emitting diodes with different spectral emission characteristics, in particular so as to simulate the ultraviolet spectral component of natural solar radiation. This makes it possible to ensure that the UV-A component and the UV-B component of the solar spectrum are taken into account in a consistently realistic way. Since the different types of light-emitting diodes can also be operated individually, it is also possible to study the effect of exposing the material samples to individual wavelength ranges.

It is furthermore possible to provide at least one other type of light-emitting diode in addition, the spectral emission of which lies in the visible spectral range so that, in particular, part of the visible spectral component of natural solar radiation can also be simulated. If desired, essentially the entire spectrum of natural solar radiation can be covered in this way by providing different types of LEDs with different emission characteristics.

The LED arrangement is preferably provided as a regular arrangement of the LEDs, i.e. in particular in the form of a matrix of rows and columns.

It may be necessary to expose material sample which has a non-planar surfaced topology. In this case, the LED arrangement may be designed and arranged so that the LEDs face the sample surface of the material sample with an equal distance, so as to achieve uniform exposure of the material sample. If a plurality of material samples are being exposed, then it is equally well possible to provide the LEDs at equal distances from the sample surfaces of the plurality of material samples. The LED arrangement can accordingly be adapted to the profile or topology of the single sample surface, or of the plurality of sample surfaces.

In particular, it may be possible to adapt the LED arrangement by mounting the LEDs on flexible printed circuit board, in particular a so-called flexboard. The mounting may be carried out in a manner which is known per se by using surface mount technology (SMT), with a multiplicity of LEDs being mounted on a printed circuit board (PCB). It is then possible to use an LED design which, for example, is described in the article "Siemens SMT TOPLED for surface mount technology" by F. Möllmer and G. Wait1 in the journal Siemens Components 29 (1991), volume 4, page 147 in conjunction with Illustration 1. This form of LED is extremely compact and makes it possible to arrange a multiplicity of such LEDs in a row or matrix arrangement.

If the LEDs are mounted on a flexible printed circuit board, then this may be supported by fitting it to a holding body so that it adopts the surface shape and topology of the latter. This holding body may consist of a thick metal plate, so that it simultaneously acts as a heat sink. The metal plate, or another support, may be pliable in a geometrically stable way so that it is possible to adapt to modified sample shapes. The holding body then needs to be fastened to an inner wall of the weathering chamber.

As an alternative to this, a flexible printed circuit board itself may be designed, in terms of its thickness and its material, in such a way that it is pliable and respectively maintains the new state in a geometrically stable way.

In a conventional weathering tester, the sample holding means are formed by a holding frame closed in a ring shape, which extends concentrically around the radiation source and, in particular, to which a rotational movement around the radiation source can be imparted. If the present invention is to be used in a conventional weathering tester, then the LED arrangement may be provided inside the ring-shaped holding frame, likewise as an arrangement closed in a ring shape. In particular, a tubular holding body may be provided inside the holding frame and concentrically with it, the LEDs being fastened in a desired distribution on the outer circumference of the tubular holding body and electrically connected in a suitable way. The LEDs are preferably mounted on a flexible printed circuit board which is in turn placed on the outer circumference of the tubular holding body and fastened to it. The tubular holding body may be made of a metal, so that it constitutes a heat sink for dissipating heat from the LEDs.

The present invention will be explained in more detail below with reference to exemplary embodiments in conjunction with the figures of the drawing, in which:

FIG. 1 represents a longitudinal section of a device according to the invention for the artificial weathering of samples.

Figure 1:
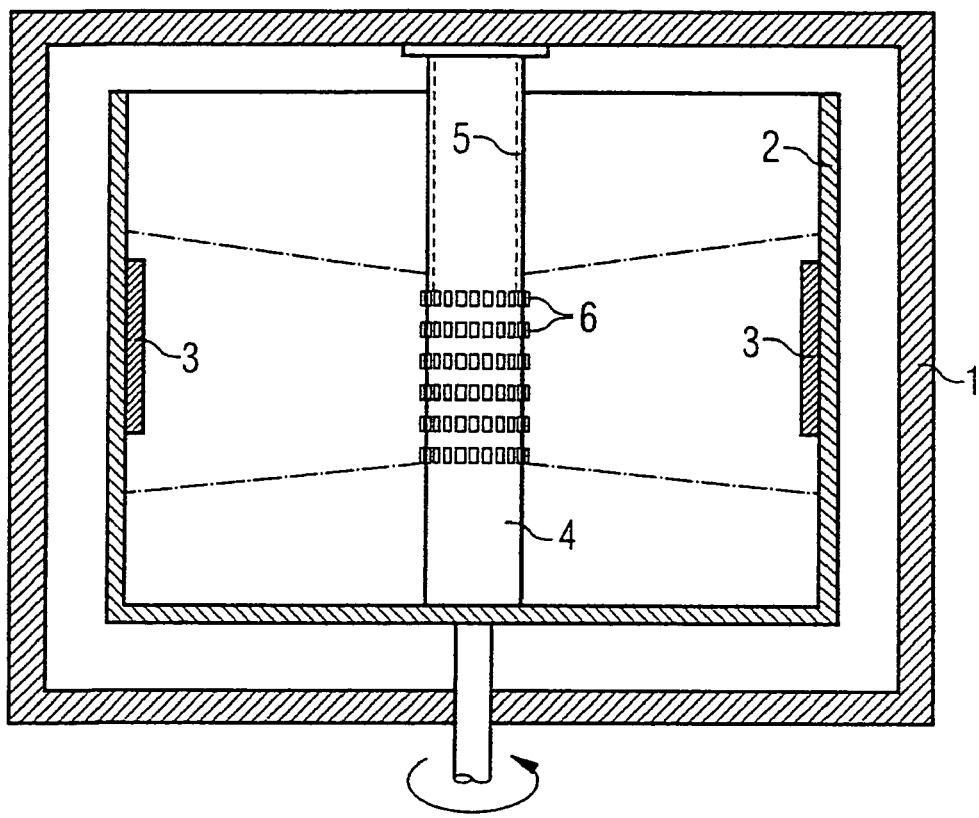
FIG. 1 shows a longitudinal section of an exemplary embodiment of a device according to the invention for the artificial weathering of samples.

A holding frame 2 closed in a ring shape is mounted so that it can rotate in a weathering chamber 1, and samples 3 or work-pieces can be held on its inner wall. The holding frame 2 has, in particular, a circular cross section. A tubular holding body 4 is positioned inside the holding frame 2 and concentrically with it, by fixing it to the upper wall of the weathering chamber 1. A flexible printed circuit board 5 is placed around the outer circumference of the tubular holding body 4 and is fastened to it in a suitable way. UV light-emitting diodes 6 are mounted on a regular arrangement on the flexible printed circuit board 5 by using surface mount technology. These may comprise different types of light-emitting diodes with different spectral emission characteristics. They may furthermore be electrically operated individually, and each individual light-emitting diode may be operated in a variable way as a function of time. Also, light-emitting diodes of one spectral type may be electrically operated together and light-emitting diodes of another spectral type may likewise be electrically operated together. The entire field of light-emitting diodes may be divided into a number of sub-fields, each sub-field containing at least one light-emitting diode of each spectral type to be used.

The holding frame 2 is preferably mounted so that it can rotate in such a way that the rotation axis coincides with the axis of the tubular holding body 4, so that the samples 3 move on a circular path around the individual light-emitting diodes 6 and at an equal distance from them.

In a manner which is known per se, the weathering chamber 1 may also have other artificial weathering instruments, for example moisture generators or the like, although these do not play an essential part in the present invention and will not therefore be discussed in detail. For example, an air flow may also be blown into the weathering chamber 1 and sweep past the samples 3 in a vertical direction.

Figure 2:
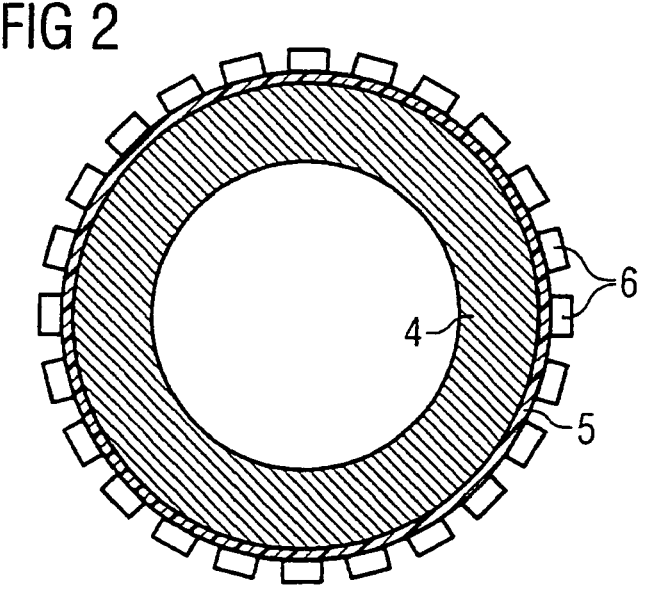
FIG. 2 shows a cross section of the tubular holding body shown in FIG. 1 with, fastened to it, the flexible printed circuit board which carries the light-emitting diodes.
Figure 3:
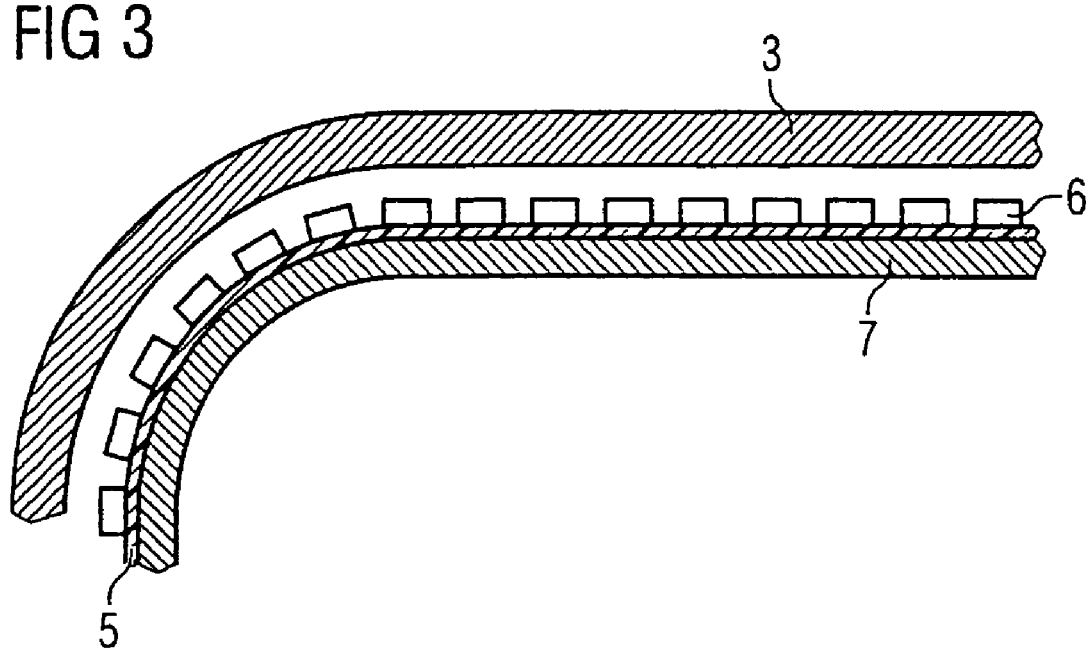
FIG. 3 shows a flexible printed circuit board which is fastened to a pliable support and carries the light-emitting diodes.

FIG. 2 represents a cross section of the tubular holding body 4 in FIG. 1. The flexible printed circuit board 5 is form-fitted around the outer circumference of the tubular holding body 4. The UV light-emitting diodes 6 are applied to it by using the SMT mounting technology which is known per se. This will not be described in detail because it is known in the prior art. The tubular holding body 4 may be made of a metal or another material with good thermal conductivity, so that the heat produced in the light-emitting diodes 6 can be dissipated efficiently. Optionally, the air flow produced in the weathering chamber 1 may also be passed through the interior of the tubular holding body 4 in order to dissipate the heat from it.

As shown, the LEDs 6 are arranged in a matrix. Instead of this, the rows may also be arranged alternately with an offset between LEDs that lie above one another, with one LED respectively being placed level with the gap between the two LEDs arranged in the row above.

The dynamic electrical operability of the individual light-emitting diodes may, for example, may be used for energysaving operation of the UV radiation arrangement. Specifically, for example, if only a relatively small number of material samples are to be artificially weathered, then they may be fastened next to one other on the holding frame 2 over a particular limited angular sector of it. When the holding frame 2 is set in rotation, then only those light-emitting diodes which lie in the relevant angular sector are always supplied with current, so that the material samples are exposed to the light-cone of UV radiation moving around at an angular speed which is the same as the angular speed of the holding frame 2. It is merely necessary to provide suitable electrical operation and programming of the light-emitting diodes 6.

As mentioned above, the entire diode field of the light-emitting diodes 6 may be divided into sub-fields which respectively contain at least one light-emitting diode of a particular spectral type. Spectrally different light-emitting diodes may be arranged in each of these sub-fields, so that radiation approximately comparable to the solar spectrum can be emitted.

Figure 4:
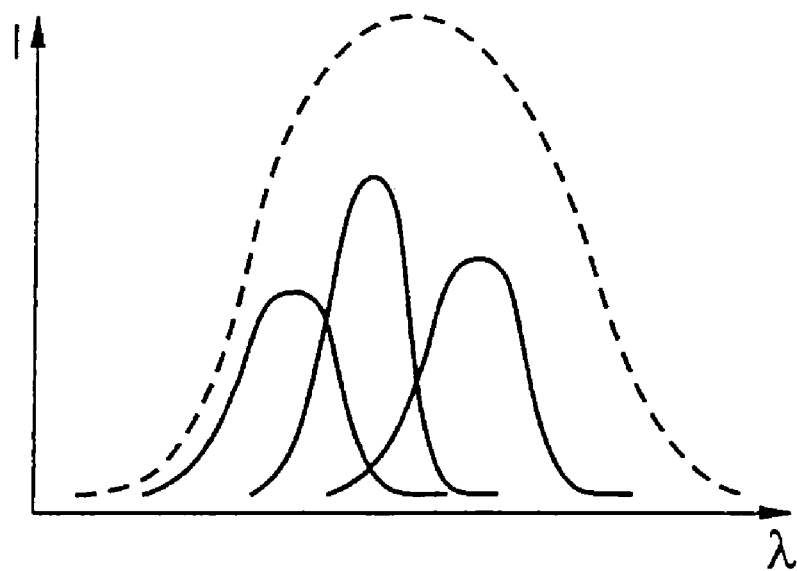
FIG. 4 shows an exemplary embodiment of the use of three different UV LEDs and their spectral emission characteristics (solid lines) and the cumulative spectral emission curve (broken line).

But if only the UV component of the solar spectrum is to be approximately simulated, for example, then three different light-emitting diodes with three different emission curves in the UV spectrum may be used. This is represented in FIG. 4 where, by way of example, the emission curves of three spectrally different light-emitting diodes which add up to give an overall emission curve are plotted between the wavelengths 300 nm and 400 nm. Since the three light-emitting diodes can be operated independently of one another, the emitted UV spectrum can therefore be adjusted flexibly.

The way in which a conventional weathering tester may be constructed according to the invention was described with reference to FIG. 1. An important point of the present invention goes beyond this, however, since it permits spatial adaptation of the UV radiation arrangement to one or more of the material samples to be exposed. This is shown in FIG. 4 by way of example in relation to a material sample 3 which has a particular surface topology. The invention now makes it possible to expose this material sample 3 in such a way that the distance between the light-emitting diodes 6 and the sample surface is spatially constant. In order to do this, the light-emitting diodes 6 are fastened on a flexible printed circuit board 5 in the manner already described above. Since in general the flexible printed circuit board 5 itself is not geometrically stable, it is applied to a substrate 7 whose shape can be altered and which keeps the shape when it is changed, that is to say it is geometrically stable. The substrate 7 may, for example, be a lightweight pliable metal sheet which again acts simultaneously as a heat sink for the heat to be dissipated from the light-emitting diodes 6. The substrate 7 then merely needs to be fastened in a suitable way on the inner wall of the weathering chamber. It is also conceivable to use a flexible printed circuit board which can be altered in a geometrically stable way owing to the way in which it is constructed, so that it is unnecessary to use an additional substrate 7.

If a rotational movement is imparted to the material sample 3 in FIG. 4, then the LED arrangement may likewise be moved in co-rotation with the same angular speed, so that the material sample 3 and the LED arrangement are always in a constant spatial relation to one another.

The invention claimed is:

1. Device for the artificial weathering of samples, having a weathering chamber (1) which contains holding means (2) for holding samples (3) to be weather and a UV radiation arrangement for applying UV radiation to the samples, characterized in that
   the UV radiation arrangement comprises an arrangement of UV light-emitting diodes (LEDs) (6).
2. Device according to claim 1, characterized in that
   a plurality of different types of light-emitting diodes (6) with different spectral emission characteristics are provided so as to simulate the ultraviolet spectral component of natural solar radiation.
3. Device according to claim 1 or 2, characterized in that
   at least one other type of light-emitting diode is also provided, the spectral emission of which lies in the visible spectral range so as to simulate part of the visible spectral component of natural solar radiation.
4. Device according to claim 3, characterized in that
   the various types of LEDs (6) essentially cover the entire spectrum of natural solar radiation.
5. Device according to claim 1, characterized in that
   the LED arrangement is provided as a regular arrangement of the LEDs (6).
6. Device according to claim 1, characterized in that
   the LED arrangement is designed and arranged so that the LEDs (6) face the sample surface of a sample (3) or the sample surfaces of a plurality of samples with an equal distance.
7. Device according to claim 6, characterized in that
   the LED arrangement is designed so that it can be adapted to the profile of the single sample surface or of the plurality of sample surfaces.
8. Device according to claim 1, characterized in that
   the LEDs (6) are mounted on a flexible printed circuit board (5).
9. Device according to claim 8, characterized in that
   the flexible printed circuit board (5) is fastened on a holding body (4; 7) which is designed as a heat sink.
10. Device according to one of the preceding claims, characterized in that
    the holding means (2) are formed by a holding frame (2) closed in a ring shape, which extends concentrically around the radiation source and to which a rotational movement around the radiation source can be imparted.
11. Device according to claim 10, characterized in that
    the LED arrangement is provided as an arrangement closed in a ring shape inside the holding frame (2).
12. Device according to claim 11, characterized in that
    the LED arrangement or a flexible printed circuit board (5), on which the LEDs (6) are fastened, is fastened to a tubular holding body (4) which is designed as a heat sink.
13. Device according to one of the preceding claims, characterized in that
    the LEDs (6) can be operated individually as a function of time.
14. Device according to one of the preceding claims, characterized in that
    the LEDs (6) are made on the basis of GaN.

* * * * *